United States Patent
Danson et al.

(10) Patent No.: US 10,448,887 B2
(45) Date of Patent: Oct. 22, 2019

(54) BIOMETRIC CUSTOMER SERVICE AGENT ANALYSIS SYSTEMS AND METHODS

(71) Applicant: Mattersight Corporation, Chicago, IL (US)

(72) Inventors: Christopher Danson, Austin, TX (US); William Duane Skeen, Austin, TX (US)

(73) Assignee: MATTERSIGHT CORPORATION, Chicago, IL (US)

( * ) Notice: Subject to any disclaimer, the term of this patent is extended or adjusted under 35 U.S.C. 154(b) by 32 days.

(21) Appl. No.: 15/335,006

(22) Filed: Oct. 26, 2016

(65) Prior Publication Data

US 2018/0110460 A1    Apr. 26, 2018

(51) Int. Cl.

| | |
|---|---|
| *A61B 5/0402* | (2006.01) |
| *A61B 5/00* | (2006.01) |
| *G09B 5/00* | (2006.01) |
| *A61B 5/0205* | (2006.01) |
| *A61B 5/1171* | (2016.01) |
| *G06Q 30/00* | (2012.01) |
| *A61B 5/021* | (2006.01) |
| *A61B 5/024* | (2006.01) |
| *A61B 5/053* | (2006.01) |

(Continued)

(52) U.S. Cl.
CPC ............ *A61B 5/486* (2013.01); *A61B 5/0022* (2013.01); *A61B 5/021* (2013.01); *A61B 5/02055* (2013.01); *A61B 5/02405* (2013.01); *A61B 5/0402* (2013.01); *A61B 5/0531* (2013.01); *A61B 5/1176* (2013.01); *A61B 5/14542* (2013.01); *A61B 5/742* (2013.01); *G06Q 30/016* (2013.01); *G09B 5/00* (2013.01); *G16H 10/60* (2018.01); *G16H 50/30* (2018.01); *A61B 5/0077* (2013.01); *A61B 5/02438* (2013.01); *A61B 5/0816* (2013.01); *A61B 2503/12* (2013.01)

(58) Field of Classification Search
CPC ....... H04M 2203/403; H04M 2203/40; H04M 2203/401; H04M 2203/402
See application file for complete search history.

(56) References Cited

U.S. PATENT DOCUMENTS

| | | |
|---|---|---|
| 5,299,260 A | 3/1994 | Shaio |
| 5,825,869 A | 10/1998 | Brooks et al. |

(Continued)

OTHER PUBLICATIONS

Neumann, David L. et al., "Chapter 4: The Psychophysiological Measurement of Empathy," *Psychology Empathy*, Ed. Danielle J. Scapaletti, Nova Science Publishers, 2011, pp. 1-24, available at http://www9S.griffith.edu.au/dspace/bitstream/handle/10072/44076/77247_1.pdf?sequence=1.

(Continued)

*Primary Examiner* — Bruk A Gebremichael
(74) *Attorney, Agent, or Firm* — Haynes and Boone, LLP

(57) ABSTRACT

Devices, systems, and methods to receive and analyze biometric measurements from a customer service agent are provided. The analysis of the biometric measurements may be used to identify correlations between the biometric measurements, agent health, and agent performance. These correlations may then be used to route communications to the agent and/or modify the performance and/or increase the heath of the agent. The biometric measurements may also be correlated to an empathy level of the agent.

20 Claims, 5 Drawing Sheets

(51) Int. Cl.
*A61B 5/145* (2006.01)
*G16H 50/30* (2018.01)
*G16H 10/60* (2018.01)
*A61B 5/08* (2006.01)

(56) References Cited

U.S. PATENT DOCUMENTS

| | | | |
|---|---|---|---|
| 6,002,760 | A | 12/1999 | Gisby |
| 6,603,854 | B1 | 8/2003 | Judkins et al. |
| 6,611,590 | B1 | 8/2003 | Lu et al. |
| 6,724,887 | B1 | 4/2004 | Eilbacher et al. |
| 7,151,826 | B2 | 12/2006 | Shambaugh et al. |
| 7,684,556 | B1 | 3/2010 | Jaiswal |
| 7,769,160 | B1 | 8/2010 | Cordell et al. |
| 7,809,127 | B2 | 10/2010 | Hackbarth, Jr. et al. |
| 8,130,935 | B1 | 3/2012 | Coughlan et al. |
| 8,340,274 | B2 | 12/2012 | Saushkin |
| 8,498,403 | B1 * | 7/2013 | Coughlan ............ H04M 3/5233 379/265.06 |
| 8,594,310 | B2 | 11/2013 | Desai et al. |
| 8,654,937 | B2 | 2/2014 | Agapi et al. |
| 9,167,095 | B1 | 10/2015 | Selvin et al. |
| 9,247,056 | B2 | 1/2016 | Mandalia et al. |
| 2005/0163302 | A1 | 7/2005 | Mock et al. |
| 2006/0062374 | A1 | 3/2006 | Gupta |
| 2006/0104433 | A1 | 5/2006 | Simpson et al. |
| 2007/0201684 | A1 * | 8/2007 | Boghani ............ H04M 3/5233 379/360 |
| 2009/0103709 | A1 * | 4/2009 | Conway ............ H04M 3/5175 379/265.09 |
| 2011/0263946 | A1 * | 10/2011 | el Kaliouby ......... A61B 5/1128 600/300 |
| 2013/0012788 | A1 * | 1/2013 | Horseman ........... G06F 19/3418 600/301 |
| 2014/0140496 | A1 | 5/2014 | Ripa et al. |
| 2014/0140497 | A1 * | 5/2014 | Ripa .................. H04M 3/5133 379/265.06 |
| 2014/0211933 | A1 * | 7/2014 | Vymenets .......... H04M 3/5183 379/265.06 |
| 2014/0278455 | A1 * | 9/2014 | Chandrasekaran ........................ G06Q 30/0203 705/2 |
| 2015/0271329 | A1 | 9/2015 | Deshmukh et al. |

OTHER PUBLICATIONS

Misiaszek, Tessa G., "The Psychology of Empathy," Empathetics, Nov. 5, 2015, available at http://www.slideshare.net/Mattersite/the-psychology-of-empathy.

Marr, Bernard et al., "Managing and Measuring for Value: The Case of Call Centre Performance," University School of Management, Jan. 26, 2016, pp. 3-4, available at https://dspace.lib.cranfield.ac.uk/bitstream/1826/1221/1/callcenterperformance.pdf.

* cited by examiner

BIOMETRIC CUSTOMER SERVICE AGENT ANALYSIS SYSTEMS AND METHODS

TECHNICAL FIELD

The present disclosure generally relates to devices, systems, and methods to receive biometric measurements from an agent and identify correlations between the biometric measurements and performance. These correlations may then be used to route communications to the agent and increase the performance and/or heath of the agent. The biometric measurements may also be correlated to an empathy level.

BACKGROUND OF THE DISCLOSURE

Customer service centers (also known as call centers) handle large loads of communications from a variety of sources. To more effectively handle these communications, efforts to improve efficiency often center on the performance of customer service agents as they deal with these communications. Along with other performance metrics, these efforts may include collecting biometric measurements from agents during their handling of communications, such as blood pressure and heart rate.

However, biometric measurements are often difficult to collect during an agent's handling of communications. The collection of biometric measurements itself may interfere with the agents' work and decrease performance levels. Furthermore, the use of biometric measurements is generally limited to tracking basic stress levels via limited measurements such as blood pressure and heart rate in existing efficiency improvement systems. Another problem with the collection of biometric measurements is that correlations between biometric measurements and agent performance are not well understood.

Furthermore, recent advances in psychophysiological studies have pointed to methods to objectively measure empathy levels of individuals. Agents who are perceived to be "empathetic" often receive higher performance scores. However, biometric measurements are not correlated to an empathy level in existing efficiency improvement systems.

Accordingly, needs exist to collect more types of biometric measurements from agents, correlate biometric measurements to performance, and use this correlation to increase the performance and/or health of agents.

SUMMARY

The present disclosure describes methods and systems that measure and analyze agent biometric data. In some embodiments, a method of routing a communication with a customer in a customer service center is provided, which includes: routing a customer communication to a customer service agent; receiving biometric data for the agent that is measured in association with the customer communication; creating a biometric analysis based on comparing the measured biometric data to a plurality of pre-set biometric data parameters; determining a performance score based on the agent's performance in interacting with the customer during the communication; correlating the biometric analysis to the performance score; creating a performance recommendation for modifying performance of the agent in one or more future communications; and providing a routing recommendation for the one or more future communications based on the performance recommendation.

In some embodiments, the measured biometric data include one or more of a blood pressure, a heart rate, a heart rate variability, a blood oxygen level, a breath rate, an electrocardiogram (EKG) reading, a skin temperature, a skin conductance, and a facial expression. The method may also include measuring the biometric data with a biometric measurement device associated with the customer service agent. In some embodiments, the biometric measurement device is configured to be worn on an arm of the agent.

The method may also include displaying the performance recommendation to a user. The performance recommendation may include an action to increase a health score of the agent. The method may also include correlating the biometric data to an empathy score for the agent. The performance recommendation may include an action to increase the empathy score of the agent.

In some embodiments, the method may include displaying the routing recommendation to a user, or distributing the routing recommendation to a contact center for routing a customer to an agent during one or more future communications. The user may be the agent, a supervisor of the agent, or a medical practitioner, or a combination thereof.

A method for creating recommendations to beneficially modify the health of a contact center agent is also provided, which includes: routing one or more customer communications with a customer to the agent; receiving measurements of biometric data for the agent taken while the agent interacts with the customer; creating a health recommendation to beneficially modify an aspect of the agent's health; and displaying the health recommendation to a user.

The method may also include providing a routing recommendation for one or more future communications based on the health recommendation or determining a health score based on the biometric data. The health score may include a stress level assessment, an overall health assessment, or both. The biometric data may include one or more of a blood pressure, a heart rate, a heart rate variability, a blood oxygen level, a breath rate, an electrocardiogram (EKG) reading, a skin temperature, a skin conductance, and a facial expression.

A system to modify performance of contact center agents based on measured biometric attributes is also provided, which includes: a biometric measurement device including one or more biometric sensors configured to measure one or more biometric attributes of a contact center agent; an analysis processor in communication with the biometric measurement device, wherein the analysis processor is operably connected to a non-transitory computer readable medium which includes a plurality of instructions stored in association therewith that are accessible to, and executable by, the processor, wherein the plurality of instructions when executed: receive the one or more biometric attributes from the one or more biometric sensors during a communication with a customer; determine a performance score based on an agent interaction with the customer during the communication; correlate the performance score of the agent to the one or more biometric attributes; provide a performance recommendation based on a comparison of the performance score and the one or more biometric attributes; and provide a routing recommendation for one or more future communications for the agent based on the performance recommendation.

In some embodiments, the system may include a display device configured to display the performance recommendation to a user. The one or more biometric attributes may include one or more of a blood pressure, a heart rate, a heart rate variability, a blood oxygen level, a breath rate, an electrocardiogram (EKG) reading, a skin temperature, a skin conductance, and a facial expression.

In some embodiments, the one or more biometric sensors include one or more of a heart rate monitor, a blood oxygen monitor, a breath rate sensor, an electrodermal analysis (EDA) sensor, a thermometer, an EKG system, a facial recognition system, and a functional magnetic resonance imaging (FMRI) system. The biometric measurement device may be configured to be worn on an arm of the agent.

In some embodiments, the plurality of instructions further include: correlating the one or more biometric attributes to an empathy score; comparing the empathy score to the performance score; and providing an empathy recommendation based on a comparison of the empathy score to the performance score, wherein the empathy recommendation is based on increasing the empathy score. The plurality of instructions may also include providing a routing recommendation for one or more future communications based on the empathy recommendation.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
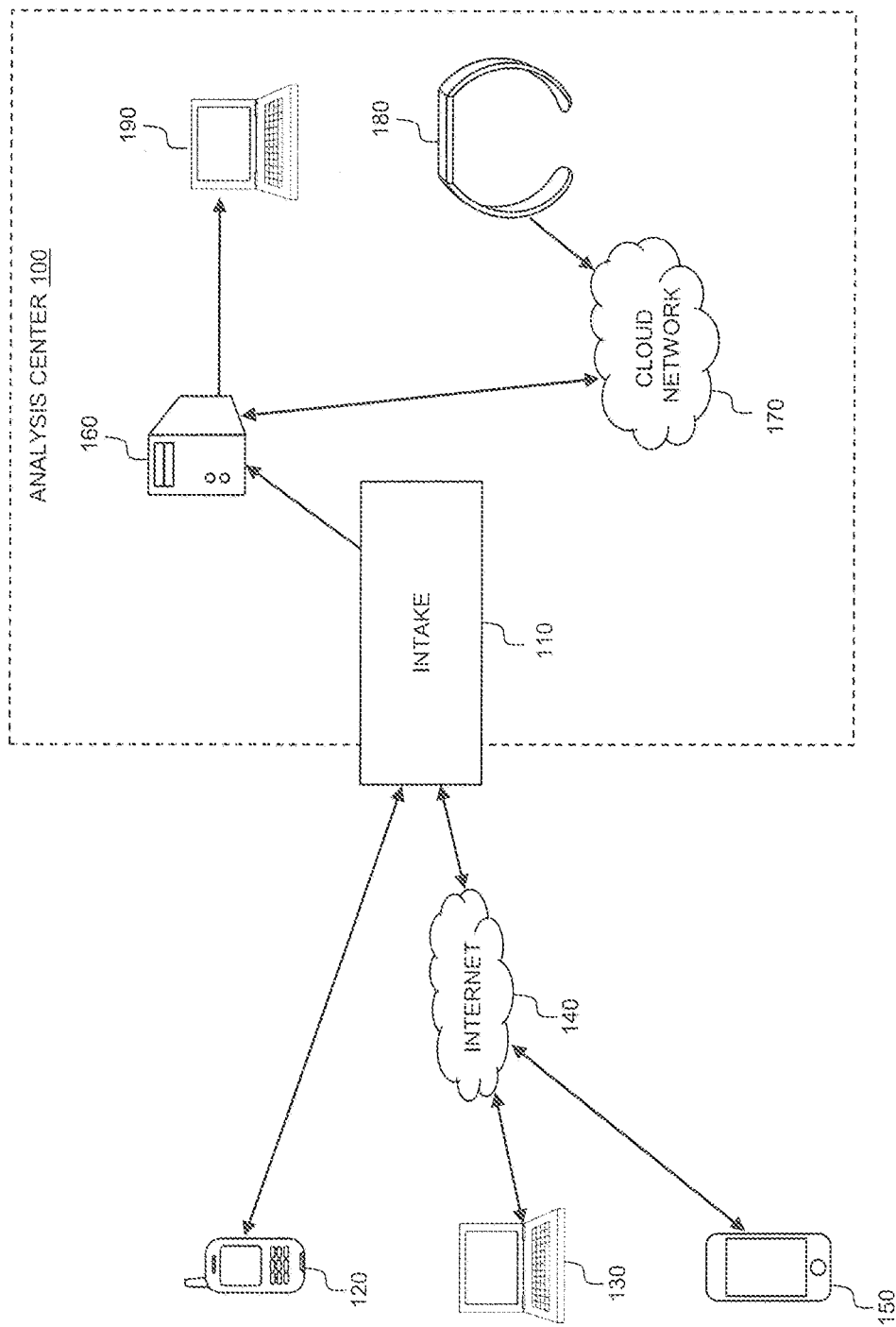
FIG. 1 is a block diagram of an embodiment of an exemplary system for receiving and analyzing communications and biometric data according to various aspects of the present disclosure.

The present disclosure advantageously describes devices, systems, and methods to receive and analyze biometric measurements from a contact center agent. The analysis of the biometric measurements may be used to identify correlations between the biometric measurements, agent health, and agent performance. These correlations may then be used to route communications to the agent, improve the performance and heath of the agent, or both. The biometric measurements may also be correlated to an empathy level of the agent.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one of ordinary skill in the art to which the disclosure relates. In particular, it is fully contemplated that the features, components, and/or steps described with respect to one embodiment may be combined with the features, components, and/or steps described with respect to other embodiments of the present disclosure. For example, although the present disclosure refers to a customer service agent, the devices, systems, and methods may be applied to any user. For the sake of brevity, however, the numerous iterations of these combinations will not be described separately.

FIG. 1 is a simplified block diagram of an embodiment of an analysis center 100 according to various aspects of the present disclosure. An analysis center 100 as described herein may include any facility or system server suitable for receiving and recording electronic communications from data sources. Such data sources may include communications on the internet, communications from customers to one or more businesses (it being understood that customers is used herein to include contacts who may become future customers), and communications between employees. In some embodiments, the analysis center 100 is a customer service center or call center. In this case, communications received by the analysis center 100 may be routed to agents based on a routing algorithm. The communications received by each agent may depend on a skill set or a work load of the agent. In some embodiments, biometric measurements of the agents of the analysis center 100 are collected during their handling of received communications.

As shown in FIG. 1, the analysis center 100 is operable to receive and record varying electronic communications and data formats. In some embodiments, an intake 110 of the analysis center 100 collects data from numerous data sources. For example, the analysis center 100 may collect data from telephones and cellular (i.e. mobile) phones 120, fax machines, computers 130, or personal computing devices 150, as well as directly scraping information from one or more websites or other information on the Internet 140. Further, the analysis center 100 may accept internet-based interaction sessions from computers 130, VoIP telephones, and personal computing devices 150 such as internet-enabled smartphones and tablets, and personal digital assistants (PDAs). These data sources generally include voice and non-voice data. Other data sources may include video interactions, facsimile transmissions, e-mails, web interactions, texts, chats, and voice over IP ("VoIP"). These communications may occur on public switched telephone network (PSTN) or the Internet, e.g., including via Skype®, Facetime®, Tango™, or any other communication app, program, website, or other software or hardware. Various specific types of communications contemplated through one or more of these channels include, without limitation, email, SMS data (e.g., text), tweet, instant message, web-form submission, smartphone app, social media data, and web content data (including but not limited to internet survey data, blog data, microblog data, discussion forum data, and chat data), etc. In some embodiments, the communications may include customer tasks, such as taking an order, making a sale, responding to a complaint, etc. It is contemplated that these data sources may be transmitted by and through any type of telecommunication device and over any medium suitable for carrying such data. For example, the data sources may be transmitted by or through telephone lines, cable, or wireless communications (e.g., satellite, Wi-Fi, Bluetooth, cellular phone network, etc.).

In one preferred embodiment of this disclosure, irrespective of other data collected by the customer analysis center 100, a portion of the data received is in the form of one or more customer communications with a contact center agent. In other embodiments, however, the data is collected and stored in association with each customer, and then used according to the disclosure during the current customer communication with the contact center agent.

In some cases, the intake 110 is configured to convert data streams with analog data, such as audio or voice data, into a digital format. In some cases, the data streams are converted into binary or text-based forms. Furthermore, the conversion of digital data to words and terms may occur at an analysis control center 160. The digitized data may be communicated to the cloud network 170 and the display 190.

As one of ordinary skill in the art would recognize, the communication channels associated with an analysis center 100 illustrated in FIG. 1 are just an example, and the analysis center 100 may accept other data from other sources, through various additional and/or different devices and communication channels whether or not expressly described herein. For example, in some embodiments, internet-based interactions, video-based interactions and/or telephone-based interactions may be routed through a customer service center, such as a call center or fulfillment center, before reaching the analysis center 100. It should be understood that such a customer service center may include stand-alone or third-party service centers or proprietary service centers (e.g., staffed with employees or consultants for a particular company, such as a computer vendor, airline, social media app, hotel chain, etc.). These interactions may also be routed simultaneously to the analysis center 100 and the customer service center (or even directly and only to the analysis center 100, in some embodiments to be distributed to a customer service center after analysis according to the disclosure herein). In some instances, the customer service center captures interaction data relevant to the analysis center 100, and applies computer-implemented linguistic algorithms to the data to generate digital data for the analysis center 100. In other embodiments, the analysis center 100 applies such algorithms and generates digital data for analysis. Further, the customer service center may be a part of, or independent of, the analysis center 100. In other embodiments, the analysis center 100 is associated with one or more customer service centers and provides output, e.g., the routing recommendations and/or biometric related recommendations, to one or more of the customer service centers to be implemented.

The analysis center 100 or associated contact center (collectively referred to in various embodiments as the analysis center) may also include a biometric measurement device 180 which is operable to receive biometric measurements from an agent. In some embodiments, the biometric measurement device 180 is configured to receive biometric measurements including blood pressure, heart rate, heart rate variability, blood oxygen levels, breath rate, electrocardiogram (EKG) readings, skin temperature, skin conductance, facial expressions, and other measurements. In some embodiments, the biometric measurement device 180 includes a device worn by the agent. In particular, the biometric measurement device 180 may be worn on the arm, neck, or head of an agent. Preferred embodiments on the agents arm include the wrist, bicep, or hand (e.g., a finger, the palm, back of the hand). The biometric measurement device 180 may include electronic wrist bands such as the Angel Sensor by Seraphim Sense Ltd. Other types of biometric measurement devices 180 may also be used by the analysis center 100, including medical systems configured to take EKG and functional magnetic resonance imaging (FMRI) readings. Furthermore, cameras may be included that are configured to analyze the posture and facial expressions of an agent. The biometric measurements may be sent by the one or more biometric measurement devices to a network within the analysis control center, such as the cloud network 170. In some embodiments, the biometric measurements received by the biometric measurement device 180 are sent to the analysis control center 160, the cloud network 170, display 190, or to an external location such as an external database or a third party biometric analysis center.

The cloud network 170 may be a network equipped with wireless communication functionality, such as an internet or Bluetooth connection. The cloud network 170 may utilize storage components that may be located at the analysis center 100 or at an external location. The cloud network 170 may facilitate the analysis of biometric measurements to and automatically send the analysis to the analysis control center 160 or other locations.

The analysis control center 160 may be generally configured to provide recording, voice analysis, data storage, data relationship analysis, biometric measurement analysis, behavioral analysis, performance analysis, health analysis, and other processing functionality to the analysis center 100. In the illustrated embodiment, the analysis control center 160 is an information handling system such as a computer, server, workstation, mainframe computer, or other suitable computing device. In other embodiments, the analysis control center 160 may be a plurality of communicatively coupled computing devices coordinated to provide the above functionality for the analysis center 100. As shown in FIG. 1, the analysis control center 160 is configured to perform analysis of data streams gathered by intake 110 as well as analysis of biometric signals received by the one or more biometric measurement devices 180.

In some embodiments, the analysis control center 160 is operable to analyze the biometric measurements received by the biometric measurement device 180, determine a performance score for the agent, and determine an empathy score for the agent. The performance score and the empathy score may be correlated to the biometric measurements by the analysis control center 160. The correlation of the various scores and biometric measurements may be used to provide recommendations to the agent and others and to provide routing recommendations for routing communications in the analysis center 100. Biometric analysis may also be used to determine a health level of the agent. This may help in identifying problems within the analysis center 100 and may be used to improve the overall health of agents.

The analysis of the biometric measurements and creation of the performance score, empathy score, and health level may include performing software instructions on received data, applying algorithms to the data, or by sorting the data in other ways. The results of the data are preferably communicated to the display 190, although it should be understood that the data may be stored first for display later, transmitted remotely for display, etc., or both. The display 190 may include an interface such as a computer screen on which a user may view analysis results, scores, and recommendations. The display 190 may also be included as an integrated component of an analysis control system 200 as shown in FIG. 2.

Figure 2:
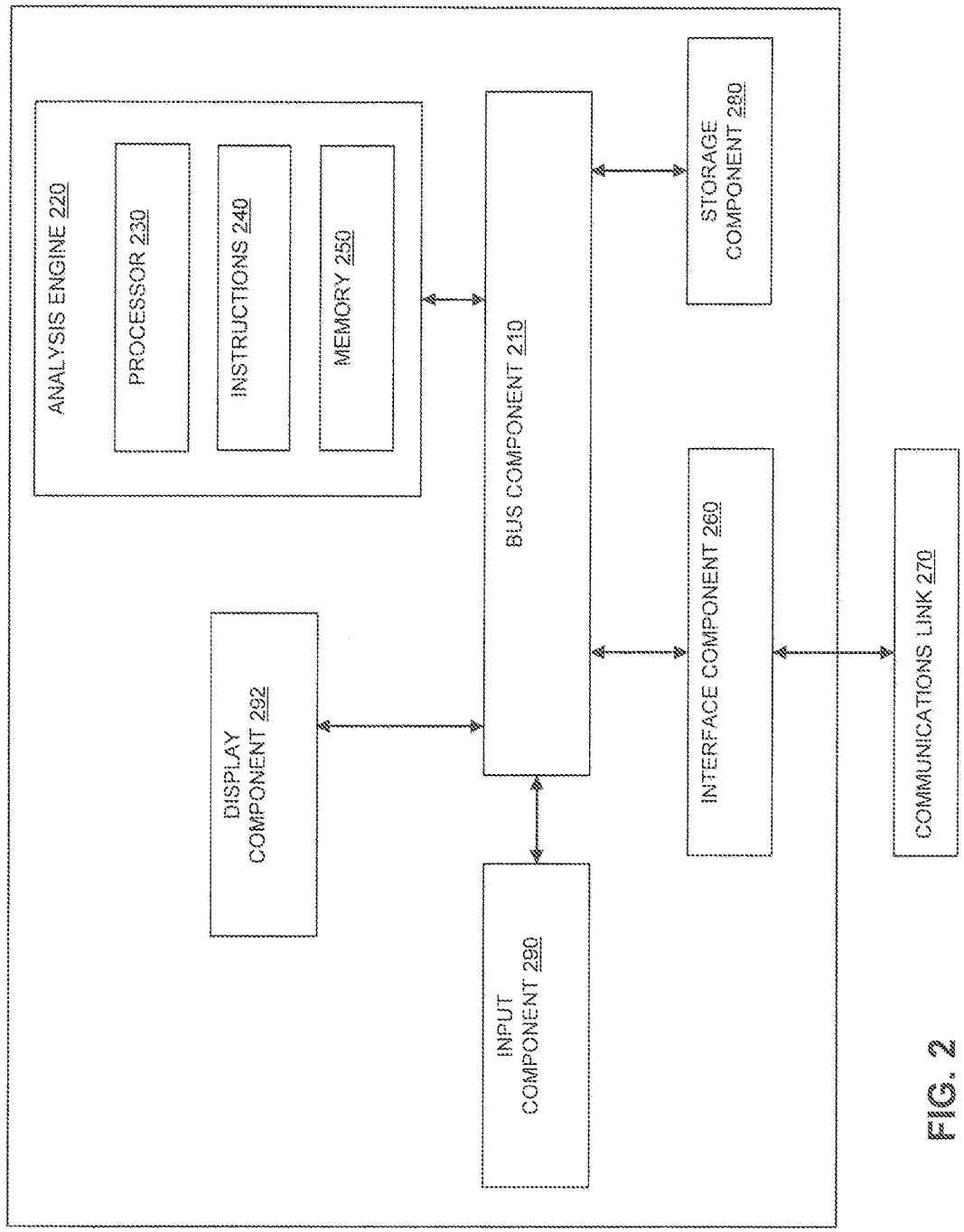
FIG. 2 is a detailed block diagram of an exemplary analysis system according to aspects of the present disclosure.

FIG. 2 shows a block diagram of an analysis control system 200 according to aspects of the present disclosure. In some embodiments, the analysis control system 200 may perform some or all of the functionality ascribed to the analysis control center 160 of FIG. 1. For instance, the analysis control system 200 may record or receive telephone, internet, and/or other interactions or communications, perform data conversion and data analysis, perform other analysis center-related computing tasks, as well as combinations thereof. In particular, the analysis control system 200 may be integrated into the analysis control center 160 as a hardware or software module and share its computing resources, such as with one or more of intake 110, cloud network 170, and display 190. Alternatively, the analysis control system 200 may be a separate computing system from the analysis control center 160.

The analysis control system 200 may be configured to analyze biometric measurements and conduct automated analysis on data streams. In particular, the analysis control system 200 may be configured to analyze a set of biometric measurements in order to make a routing recommendation. In some embodiments, the analysis control center 200 is operable to compare the biometric measurements to a performance score or an empathy score of an agent. The performance score and empathy score may be based on the performance and empathy of the agent during his or her handling of one or more communications. The analysis control system 200 may include a bus component 210, an analysis engine 220, a network interface component 260, a communications link 270, a storage component 280, an input component 290, and a display component 292. In some cases, the analysis engine 220 is configured to analyze data streams received by the analysis control system 200. The analysis engine 220 may include a processor 230 that is communicatively coupled to a memory 250, as well as a set of instructions 240.

In accordance with embodiments of the present disclosure, analysis engine 220 performs specific operations by processor 230 executing one or more sequences of one or more instructions 240 contained in memory 250. The processor 230 may be any custom made or commercially available processor, a central processing unit (CPU), an auxiliary processor among several processors associated with the analysis control system 200, a semiconductor-based microprocessor (in the form of a microchip or chip set), a macroprocessor, a collection of communicatively coupled processors, or any device for executing software instructions. The memory 250 provides the processor 230 with non-transitory, computer-readable storage to facilitate execution of computer instructions by the processor 230. Examples of memory 250 may include random access memory (RAM) devices such as dynamic RAM (DRAM), synchronous DRAM (SDRAM), solid state memory devices, and/or a variety of other memory devices known in the art.

Logic may be encoded in a computer readable medium, which may refer to any medium that participates in providing instructions 240 to processor 230 for execution. In one embodiment, the computer readable medium is non-transitory. Such a medium may take many forms, including but not limited to, non-volatile media, volatile media, and transmission media. In various implementations, volatile media includes dynamic memory, such as memory 250, and transmission media includes coaxial cables, copper wire, and fiber optics, including wires that comprise bus component 210. Memory may be used to store visual representations of the different options for searching or auto-synchronizing. In one example, transmission media may take the form of acoustic or light waves, such as those generated during radio wave and infrared data communications. Some common forms of computer readable media include, for example, RAM, PROM, EPROM, FLASH-EPROM, any other memory chip or cartridge, carrier wave, or any other medium from which a computer is adapted to read.

Furthermore, instructions 240 may be read into memory 250 from another computer readable medium, such as storage component 280. These may include instructions to receive sensor data including biometric measurements, analyze the sensor data, receive empathy data from one or more users, receive performance data from one or more users, compare the sensor data with the performance data and the empathy data, make recommendations based on the comparison of sensor data and performance data, and display the recommendations in various formats to a user. In other embodiments, hard-wired circuitry may be used in place of or in combination with software instructions for implementation of one or more embodiments of the disclosure.

Computer programs, instructions, and data may be stored on the storage component 280. The storage component 280 may include mass storage devices including hard discs, optical disks, magneto-optical discs, solid-state storage devices, tape drives, CD-ROM drives, and/or a variety of other mass storage devices known in the art. Further, the mass storage device may be implemented across one or more network-based storage systems, such as a storage area network (SAN).

Still referring to FIG. 2, the interface component 260 may be operable to receive and transmit analysis center-related data between local and remote networked systems and communicate information via the communications link 270. Examples of interface components 260 may include Ethernet cards, 802.11 WiFi devices, cellular data radios, and/or other suitable devices. The analysis control system 200 may further include any number of additional components, which are omitted for simplicity, such as input and/or output (I/O) devices (or peripherals), buses, dedicated graphics controllers, storage controllers, buffers (caches), and drivers. Further, functionality described in association with the analysis control system 200 may be implemented in software (e.g., computer instructions), hardware (e.g., discrete logic circuits, application specific integrated circuit (ASIC) gates, programmable gate arrays, field programmable gate arrays (FPGAs), etc.), or a combination of hardware and software. In some embodiments, analysis data is routed from the analysis engine 220 to an external communications distributor via the interface component 260.

The display component 292 may be configured to transmit data in a textual or graphical format, such as on a computer monitor or a portable computing device (e.g., a cellphone, a tablet device, etc.). In some cases, analysis data from the analysis engine 220 is available to be displayed in several formats, optionally even simultaneously on the display component 292. For example, the display component 292 may show a performance score alongside a list of recommendations to improve performance. Alternatively, the display component 292 is an interface to an external display.

Figure 3:
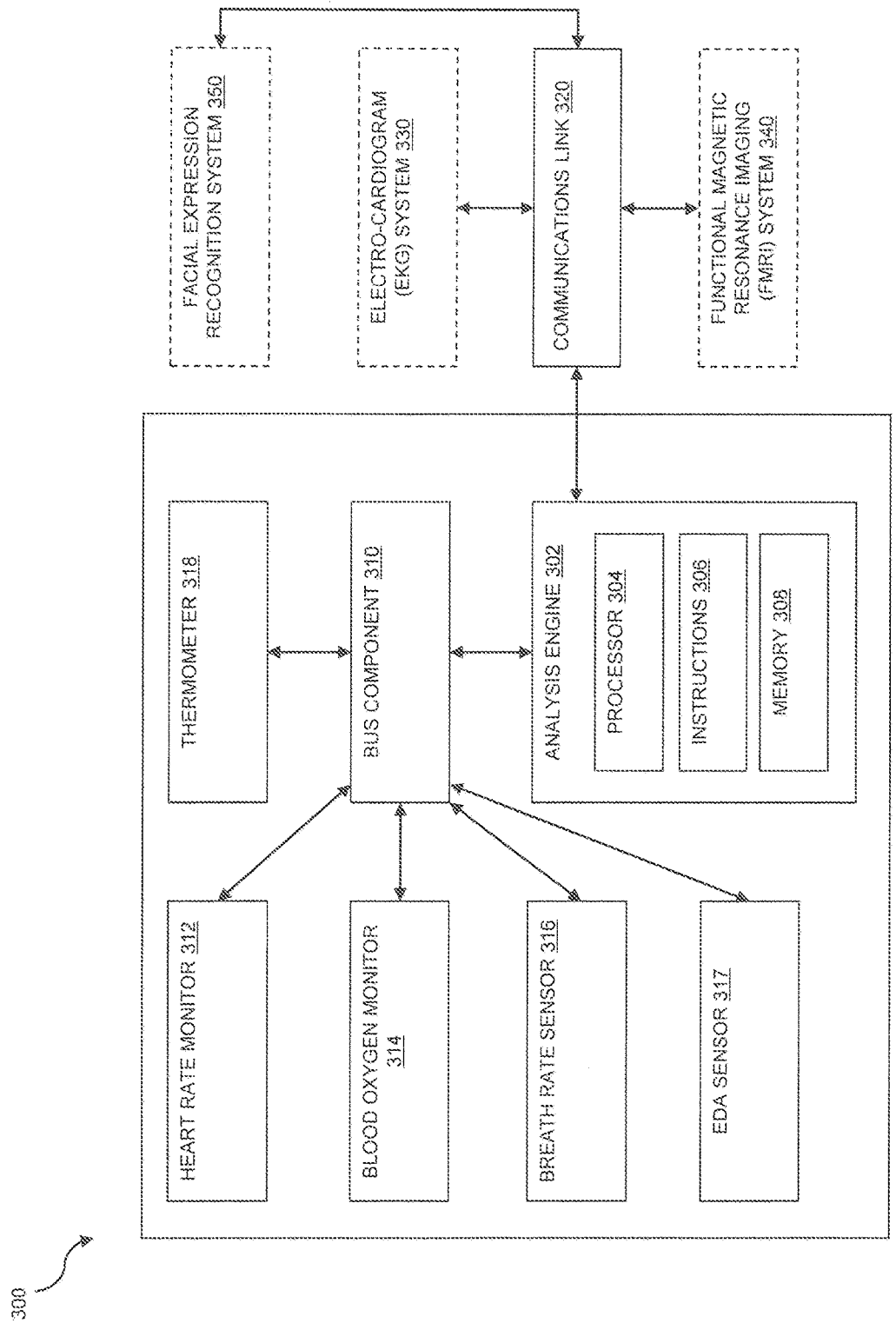
FIG. 3 is a detailed block diagram of an exemplary biometric measurement device according to aspects of the present disclosure.

FIG. 3 shows a block diagram of a biometric measurement device 300 according to aspects of the present disclosure. In some embodiments, the biometric measurement device 300 may perform some or all of the functionality ascribed to the biometric measurement device 180 shown in FIG. 1. For instance, the biometric measurement device 300 may be operable to receive biometric measurements from a user including blood pressure, heart rate, heart rate variability, blood oxygen levels, breathing rate, electrocardiogram (EKG) readings, skin temperature, skin conductance, facial expressions, and other measurements. In some embodiments, the biometric measurement device 300 is a single device that is wearable by a user. In particular, the biometric measurement device 300 may be configured to be worn by a customer service center agent during work, such as on the wrist or arm of the agent. For agents particularly interested in their health, the biometric measurement device 300 may be worn all the time (except possibly during charging), may be worn during all waking hours, or used at other times outside of work to provide additional baseline to help ensure health is being beneficially modified at work through the routing recommendations and/or performance recommendations disclosed herein. In some embodiments, the performance of the agent may be compared with an analysis of the biometric measurements received by the biometric measurement device 300. In other embodiments, the biometric measurement device 300 is a separate system from the biometric measurement device 180 and may be used in conjunction with other measurement devices.

The biometric measurement device 300 may include an analysis engine 302, a bus component 310, and, by way of a non-limiting example, a heart rate monitor 312, a blood oxygen monitor 314, a breath rate sensor 316, an electrodermal activity (EDA) sensor 317, or a thermometer 318, or a combination of any of the previous sensors, and a communications link 320. The analysis engine 302 of the biometric measurement device 300 may function similarly to the analysis engine 220 of the analysis control system 200. In particular, the analysis engine 302 may be configured to receive biometric measurements from the various sensors included within or in communication with the biometric measurement device 300.

In accordance with embodiments of the present disclosure, analysis engine 302 performs specific operations by processor 304 executing one or more sequences of one or more instructions 306 contained in memory 308. The processor 304 may be any custom made or commercially available processor. The memory 308 provides the processor 304 with non-transitory, computer-readable storage to facilitate execution of computer instructions by the processor 304. Logic may be encoded in a computer readable medium, which may refer to any medium that participates in providing instructions 306 to processor 304 for execution. The instructions 306 may include instructions to receive sensor data from various sensors within or in communication with the biometric measurement device 300, convert the sensor data to useable formats, and analyze the sensor data. In other embodiments, hard-wired circuitry may be used in place of or in combination with software instructions for implementation of one or more embodiments of the disclosure.

The bus component 310 may be configured to facilitate communication between one or more components in the biometric measurement device 300. In some embodiments, the bus component 310 includes transmission media such as coaxial cables, copper wire, and fiber optics.

The heart rate monitor 312 may be any commercially available or custom monitor configured to measure the heart rate of a user. In some embodiments, the heart rate monitor is configured to measure the heart rate optically, and may be disposed on a wrist band or other wearable device.

The blood oxygen monitor 314 may be used to measure blood oxygen saturation levels of a user. The blood oxygen monitor 314 may include one or more light-emitting devices such as light-emitting diodes (LEDs). In some embodiments, the heart rate monitor 312 and blood oxygen monitor 314 are combined into a single device.

The breath rate sensor 316 may be used to measure the breathing rate of a user. The breath rate sensor 106 may include motion sensors and/or optical sensors. In some embodiments, the breath rate sensor 316 may help to indicate health and/or stress levels of a user.

The EDA sensor 317 may be used to measure the conductive properties of skin. In some embodiments, skin conductance may be correlated with the production of sweat glands. In some cases, elevated production of sweat may show stress or an increased response to stimuli. The EDA sensor 317 may be configured to contact an extremity of the user, such as a part of the head, arm, or neck.

The thermometer 318 may be any commercially available or custom thermometer configured to measure the temperature of a user. In some embodiments, the thermometer 318 is configured to measure the skin temperature of a user. In some embodiments, skin temperature may be correlated to stress levels.

The communications link 320 of the biometric measurement device 300 may be operable to transmit and receive biometric measurement data and analysis. In some embodiments, the communications link 320 may be configured to communicate with local and remote networks, such as the cloud network 170 of FIG. 1. The communications link may be configured to transmit and receive wireless communications such as WiFi and Bluetooth signals. Alternatively or additionally, it can have a wired connection to a workstation, such as to collect data on a periodic basis such as overnight while being charged in a docking station.

The biometric measurement device 300 may be configured to include or communicate with one or more of an electro-cardiogram (EKG) system 330, a functional magnetic resonance imaging (FMRI) system 340, and a facial expression recognition system 350. The EKG system 330 may include electrodes placed on a user's body that measure electrical activity of the heart. The EKG system 330 may include a miniaturized processor as well as other components and may be configured to be used by a customer service center agent.

The FMRI system 340 may be used to measure brain activity by monitoring blood flow throughout the body and brain. The FMRI system may include a number of devices that are attached to the user. In some embodiments, circulatory system measurements are received by a sensor system and FMRI data is inferred from this data. In some embodiments, the FMRI system is in communication with the biometric measurement device 300 via a wired or wireless connection.

The facial expression recognition system 350 may be used to identify the facial expressions of a user. In some embodiments, the facial expression recognition system 350 includes one or more cameras that record the facial expressions and posture of a user throughout a time period. In some embodiments, the facial recognition system 350 is in communication with a database such as storage component 280 of FIG. 2. The database may include instructions related to detecting facial features and/or identifying facial expressions. In some embodiments, the facial expression recognition system 350 may be a geometric feature based system. In this case, the facial expression recognition system 350 may identify major face components and/or feature points from images collected by the system 350. Furthermore, the distances between the major face components and/or feature points may be calculated by the system 350 to identify facial expressions. In some embodiments, images or video collected by the facial expression recognition system 350 are transmitted to an outside source, such as an external analysis system, for recognition and analysis. The posture and facial expressions of a user may be used to indicate an emotional state, and in some cases, a stress level.

Figure 4:
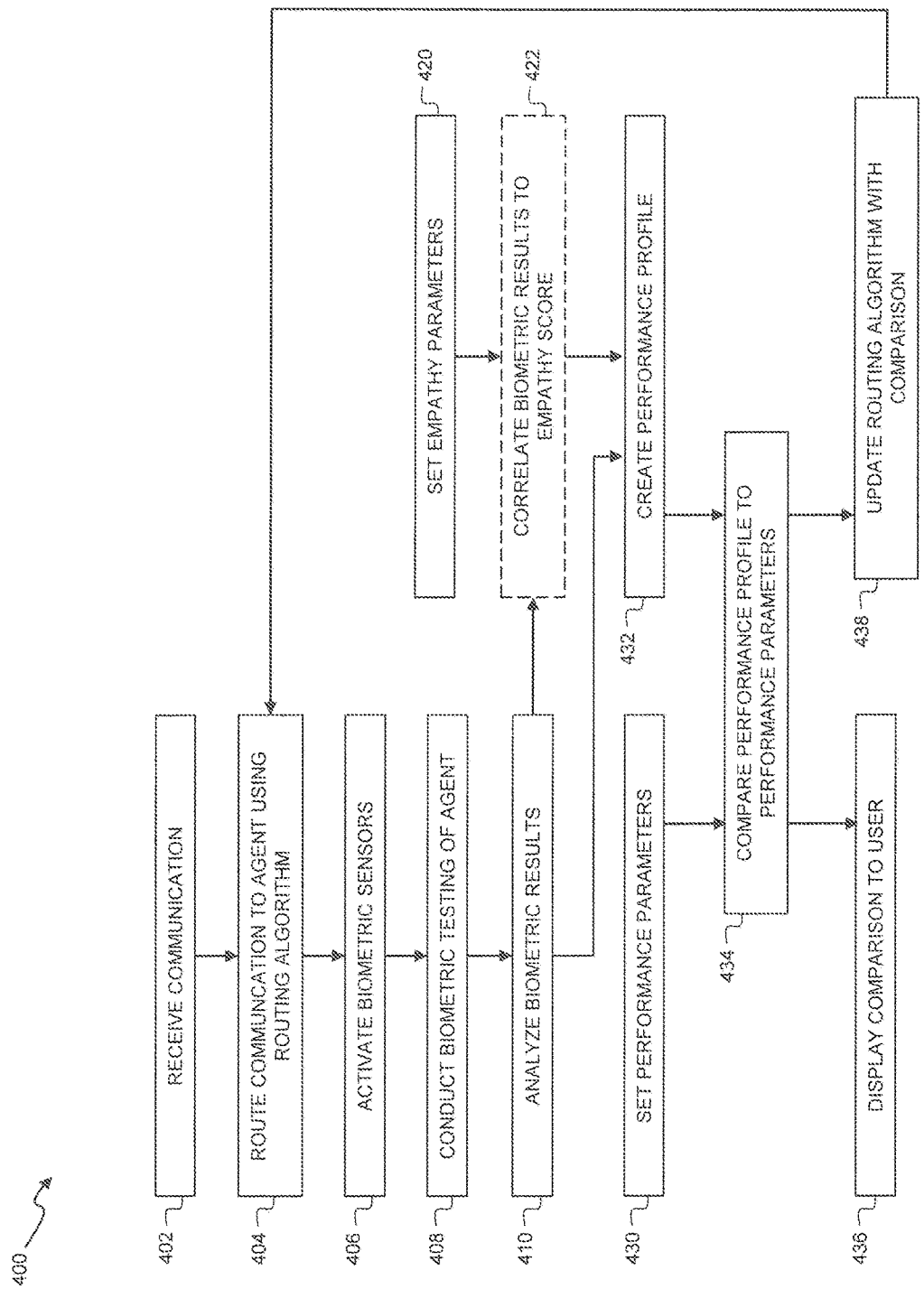
FIG. 4 is a flowchart illustrating an exemplary method of routing communications based on biometric data according to aspects of the present disclosure.

An exemplary method 400 of receiving biometric measurements and routing communications according to the disclosure is described with respect to FIG. 4. Method 400 may be performed by an analysis device such as the analysis control system 200 of FIG. 2.

At step 402, the method 400 may include receiving a communication. In some embodiments, the communication is received by an analysis system 100 such as that depicted in FIG. 1. The communication may be or may include any kind of internet-based interaction, video-based interaction and/or telephone-based interaction. The communication may include both verbal and nonverbal data. Some or all of the communication may be converted into a digital format. In some embodiments, the communication is received by a customer service center and is directed to an agent.

At step 404, the method 400 may include routing the communication to an agent using a routing algorithm. The routing algorithm may be configured to route the communication based on a number of factors, including relative workloads of various agents, skill sets of the agents, type of communication, urgency, existing relationships with agents, and other factors. In some embodiments, the routing algorithm may be configured to take into account biometric measurements of the agents. For example, communications may be routed to an agent whose biometric measurements indicate that he or she has a low stress level and/or has a high level of empathy. In other embodiments, the routing recommendations provide for communications from a particular personality type to be routed to an agent that can best handle that personality type while minimizing or avoiding an increase in stress, and in some embodiments, lowering the stress of the agent. In other embodiments, the agent and customer will have the same or another complementary personality type configuration, i.e., the agent's personality type is factored into the routing recommendation along with the customer's or a predicted customer. In all these embodiments, the level of agent empathy generally, or to a particular customer personality type, may be an input factor in the routing recommendation.

At step 406, the method 400 may include activating biometric sensors. These biometric sensors may include sensors that collect biometric information from a user. In some embodiments, the biometric sensors may include the biometric measurement device 180 as depicted in FIG. 1 or the biometric measurement device 300 as depicted in FIG. 3. In some embodiments, some or all of the biometric sensors may be included on a wearable device such as a wristband. In some embodiments, the biometric sensors may be activated before a communication is routed to the agent. For example, biometric sensors may be activated throughout a work day to provide ongoing monitoring of an agent. Furthermore, the measurements collected during the handling of two or more different communications may be compared to provide analysis of the agent's performance. Ongoing monitoring may also provide a comparison of biometric measurements during down times (which may serve as a baseline) and periods during which the agent is working. This may help to determine stress levels throughout the work day.

At step 408, the method 400 may include conducting biometric testing of the agent using the biometric sensors. In some embodiments, the biometric sensors are activated during the time that an agent receives and interacts with the communication, such as responding to a phone call, VoIP call, videoconference or video chat, or the like. The biometric sensors may also collect data during interactions between the agents and others, such as clients and other agents. The biometric sensors may be configured to assess the performance of the agent while completing a task. The biometric testing may include collecting biometric measurements such as blood pressure, heart rate, heart rate variability, blood oxygen levels, breath rate, electrocardiogram (EKG) readings, functional magnetic resonance imaging (FMRI) readings, skin temperature, skin conductance, facial expressions, and other measurements. The biometric measurements received from the biometric testing may be sent to an analysis system for analysis.

At step 410, the method 400 may include analyzing biometric measurements. This analysis may include correlating biometric measurements collected during the biometric testing of step 408 to a level of performance, a level of health, or a level of empathy. For example, the biometric testing of step 408 may include gathering video or images from a camera that show an agent's face during an interaction between the agent and a client. The video or images may be analyzed by an analysis system such as the analysis control center 160 of FIG. 1, and the analysis system may identify a number of facial expressions during the interaction, including "frustration", "confusion", and "anger." These analysis results may be recorded by various components of the system. Furthermore, the analysis results may be correlated with a heightened level of stress and a lowered level of empathy for the agent.

At step 420, the method 400 may include setting empathy parameters. In some embodiments of the present disclosure, the biometric measurements may be correlated with an empathy measurement or score of an agent. Although the term "empathy" may include a number of emotional responses, "empathy" as described herein may include one or more of the eight conceptualizations from C. D. Batson as noted by David Lester Neumann and Rae Westbury in "The Psychophysiological Measurement of Empathy" (2011), which is hereby incorporated by reference in its entirety. These conceptualizations include: (1) knowing another person's cognitive and affective internal state, (2) adopting the posture or matching the neural response of another, (3) feeling as another person feels, (4) projecting oneself into another's situation, (5) imagining the thoughts and feelings of another, (6) imagining how one would think and feel in the other's place, (7) feeling distress at witnessing another's suffering, and (8) feeling for another person who is suffering. In some embodiments, people who show empathy, or who relatively show more empathy than, e.g., another contact center agent, may communicate more effectively with others.

In some embodiments, empathy levels may be identified by the level of emotional correlation between people that are communicating. In particular, a person exhibiting a relatively higher level of empathy may exhibit very similar emotions to the person that they are communicating with. Accordingly, empathy parameters may include measuring and quantifying the emotions of the agent and as well as a person sending the communication. In the present disclosure, a contact is a person sending a communication which is received by the agent, or otherwise participating in communication between the contact and agent. In some cases, the emotional state of the contact may be assessed by aspects such as voice volume, tone, word recognition, and linguistic analysis of the communication itself. The emotional states of the contact and the agent may then be compared to assess a level of correlation.

Measuring empathy may also include analysis of a number of biometric measurements. These may include any combination of neurological signals, mimicry, emotional contagion, feedback behavior, and physiological responses to stimuli such as startle blinks and electrodermal activity, as well as other biometric measurements. Typically, without being bound by theory, the more measurements and more factors considered, the more accurate or certain the measurement.

In some embodiments, an agent may exhibit one or more neurological signals that indicate empathy. These may include activity levels in the right putamen, the left posterior/middle insula, the anterior medial cingulated cortex and the left cerebellum that have been shown in studies, such as that by Gazzola, Aziz-Sadeh, and Keysers (2006), to show a correlation to empathy. Furthermore, there may be correlation between empathetic behavior and high activity levels in areas of the brain responsible for listening, such as the auditory cortex. In some embodiments, activity levels are measured by the FMRI system 340 of FIG. 3. These activity measurements may be analyzed and correlated with an algorithm to determine an empathy level.

Mimicry may relate to similarities in the facial expressions and posture of people. For example, two people may exhibit mimicry by crossing their arms while talking, lowering their voices at the same time, and smiling at each other. In some embodiments, mimicry may be related to high listening and comprehension levels which may be strong signs of empathy. In some embodiments, mimicry is measured by identifying the posture and facial expressions of the agent with the facial expression recognition system 350 of FIG. 3. The facial expressions of the agent may be correlated to the emotional state of a contact, for example by analyzing a video communication of the contact or analyzing changes in the tone of the contact during a telephone conversation. Mimicry may be further measured by the correlation of vocal volume and tone of an agent to a contact while the agent and contact interact.

Emotional contagion and feedback behavior may refer to emotional similarities between people engaged in an interaction. For example, an agent and a contact may be communicating by telephone. Both the agent and contact may exhibit happy emotions while talking about an upcoming holiday. The contact may mention that she is worried about a problem with gifts for the holiday, and the agent may also express worry and suggest a solution. At this point, the contact may thank the agent for his suggestion with a contented tone. Similarly, the agent may express that he is happy to help. Accordingly, the high level of emotional contagion during the conversation may show that the agent is acting empathetically. Emotional contagion may be measured through analysis of interactions between agents and contacts including video and audio feeds. Furthermore, incoming communications and responses may be analyzed through linguistic analysis to measure emotional contagion. For example, the emotions of the agent and client may be shown by key words and phrases used, including "glad to help", "hopefully", and "regrettably".

In some embodiments, exhibition of various physiological responses may be correlated to a level of empathy. The physiological responses may include startle blinks and electrodermal activity. A person may exhibit startle blinks when subjected to startling or surprising stimuli. Startle blinks may also show that a person is paying attention to the stimuli, and may show that the person is listening intently. Since people that are listening closely to other are more likely to be empathetic, startle blinks may be correlated to empathy levels. Startle blinks may be measured by the facial expression recognition system 350 of FIG. 3.

Electrodermal activity (EDA) may be measured as changes in the electrical properties of the skin, such as skin conductance. In some embodiments, skin conductance has been shown in to increase as more sweat is secreted from glands within the skin. An increase in sweat production may be correlated to a degree of emotional responsiveness and attentional engagement, and therefore to a level of empathy. In some embodiments, EDA is measured by the EDA sensor 317 depicted in FIG. 3. Other physiological responses may be measured by the various systems and devices of the present disclosure. The empathy parameters of step 420 may include any of the above measurements.

At step 422, the method 400 may include correlating biometric results to an empathy score. In some embodiments, the biometric measurements of step 410 are compared to the empathy parameters of step 420. In some embodiments, the empathy score shows the level of empathy of an agent. In particular, higher empathy scores may be attributed to more empathetic behaviors. The empathy score may include sub-scores such as listening, attentiveness, responsiveness, and emotional correlation.

At step 430, the method 400 may include setting performance parameters. In some embodiments, the performance parameters may be based on the efficiency of an agent, as well as the quality of the agent's interactions. Performance parameters may include response time, quantity and rate of interactions, and quality measurements, such as surveys completed by the agents, supervisors, and contacts.

At step 432, the method 400 may include creating a performance profile for an agent. In some embodiments, the performance profile includes data from the biometric results of step 410 as well as the empathy score of step 422. The performance profile may relate to a single interaction, as well as a series of interactions. In some embodiments, the performance profile may be used to judge the performance of the agent.

At step 434, the method 400 may include comparing the performance profile to the performance parameters. The results of this step may be used to assess the performance of the agent. In some embodiments, the health of the agent may be assessed at this step. For example, the performance of an agent may be assessed during a work week. Toward the end of the week, the agent may show a significant drop in performance as well as a number of negative biometric measurements, such as an elevated heart rate and an increase in negative facial expressions. This may signal that the agent has an elevated stress level. Appropriate action may be taken by the system or the agent's supervisor to decrease workload or adjust the type of communications being routed to the agent. Another suitable action is that the system is configured to provide prompts to better coach the agent, the supervisor, or both, to minimize health risks or issues, increase health outcomes, increase agent performance while avoiding an increase in agent health risks or issues, or increase health outcomes while increasing agent performance.

The methods, apparatuses, and systems described herein may optionally also analyze comments based in part on the one or more biometric measurements that are provided by a coach relating to an agent's interaction with a customer. By way of example, the methods herein can receive a coaching comment regarding an agent's interaction with a customer, apply at least one scoring algorithm to the comment, and output a score of the scoring algorithm such as for the coach. During an in-person coaching meeting, for example, potential deficiencies in an agent's skill set can be identified, thereby leading to the assignment of various learning or training exercises or performance goals. Goals also can be assigned during a coaching meeting with any assigned learning and goals being annotated on a coaching form. In some embodiments, an agent can be given an opportunity to provide feedback on the coaching session using the coaching form. In some embodiments, a coaching session is considered complete when the corresponding coaching form is annotated as such by the relevant coach. In some embodiments, however, the coaching session may not be deemed complete until further analysis is undertaken in order to determine whether the coaching session has resulted in one or more improvements in agent performance.

At least one scoring algorithm can be applied to each comment made by the coach, either in-person or electronically. The scoring algorithm looks for: (1) specific terms and phrases that indicate the characteristic or property desired (e.g., customization, action ability, and/or encouragement), (2) the density of those terms in the overall comment; and (3) the presence of those terms in the first sentence of the comment. In certain embodiments, terms and phrases that are present in the first sentence of a coaching session, or in each section of a coaching session (e.g., covering different goals or topics like teamwork, efficiency, reliability, responsiveness, etc.) are given heavier weight than those in the rest of the comment.

In various embodiments, these terms, phrases, or keywords are stored in a library or libraries that are accessed by a control system or an analytics system. The library may separate the keywords, terms, and phrases into different categories. Keywords are the words previously determined to indicate the specific characteristic of the coaching comment. Each keyword may have respective aliases, which are essentially synonyms of keywords. Synonyms of the keywords may be identified and also stored in the library. The aliases are typically treated as interchangeable with the keywords from a scoring perspective, but in one embodiment aliases can be treated as not interchangeable if specific words, terms, or phrases are expected to be used. Also, due to the flexibility of the methods described herein, additional words, terms, and/or phrases may be added to the library at any time. For example, when it becomes apparent that another word is used frequently and is just as effective as the associated keyword, the library may be updated to include this word as an acceptable alias.

The scoring algorithm can be configured to detect keywords, terms, and phrases in the statements of the coach to the agent and the comments are scored based on the number of word hits in this embodiment. In one embodiment, the scoring algorithm includes a "customized" algorithm that looks for words that identify the specific impact that a change in behavior will have on future customer interactions and the agent's metrics. For instance, the phrases "resulting in," "help to increase," "goal is to," "saved a couple of seconds of talk time," "to decrease call length," "consequently," "as might be expected," "due to," "leads to," "brought about," "was responsible for," "to increase efficiency," "we want to decrease/increase," and "could have increased/decreased/produced/improved/saved/minimized" indicate the property of customization. In another embodiment, the scoring algorithm includes an "actionable" algorithm that looks for words that identify behavior that needs to be improved and language that is clearly indicative of what the agent needs to do next time. The "actionable" algorithm also evaluates the proximity of action words to other action words. The more action words used, the closer they are together, and the more clearly indicated the next course of action is, the higher the comment scores with the algorithm. Examples of "actionable" terms include "in the future," "make sure to," "need to work on," "remember to," and "an opportunity to." In yet another embodiment, the scoring algorithm includes an "encouragement" algorithm that looks for words that identify positive language that reinforces good behavior. Exemplary words, terms, and phrases that the algorithm searches for include "appreciate," "thanks," "thank you," "good/great/wonderful job," and "keep up the good work."

A scoring algorithm(s) is typically created by linguistic analysts and typically trained using previously analyzed coaching comments. Each algorithm is trained with known inputs and learns these patterns through one or more statistical methods. The algorithms can then properly classify new input based on the inputs it has received and processed during training. The algorithm should be able to perform accurately on new, unseen examples after having trained on a learning data set. The larger the comparable data set, the higher the accuracy the algorithm is likely to achieve. The feedback and scoring related to coaching comments can advantageously be used to provide better comments in future coaching, or training of supervisors providing such coaching comments. In various embodiments, the algorithms are calibrated, customized, and updated according to different coaching styles. Additional embodiments directed to providing coaching comments, or prompts, are disclosed in co-pending U.S. patent application Ser. No. 13/912,918, filed Jun. 7, 2013, the entire contents of which is incorporated herein by express reference thereto.

At step 436, the method 400 may include displaying the comparison of step 434 to a user. In some embodiments, the comparison is displayed to the agent as a form of feedback information. The comparison may be accompanied with a recommendation for improving performance during interactions. The comparison may be sent to a supervisor, other agents, and/or an agent database. In some embodiments, the comparison is displayed on a display device such as display 190 of FIG. 1 or display component 292 of FIG. 2.

At step 438, the method 400 may include the updating the routing algorithm with the comparison. In some embodiments, the routing algorithm is continuously updated with performance information from the agents. This may help to most efficiently route communications, as well as to improve agent wellbeing. For example, actions may be taken to improve the performance of the overstressed agent discussed in reference to step 438, such as decreasing the amount of communications routed to the agent or routing more positive communications to the agent. In some embodiments, the method 400 may repeat itself after step 438, for example, beginning at step 402.

Figure 5:
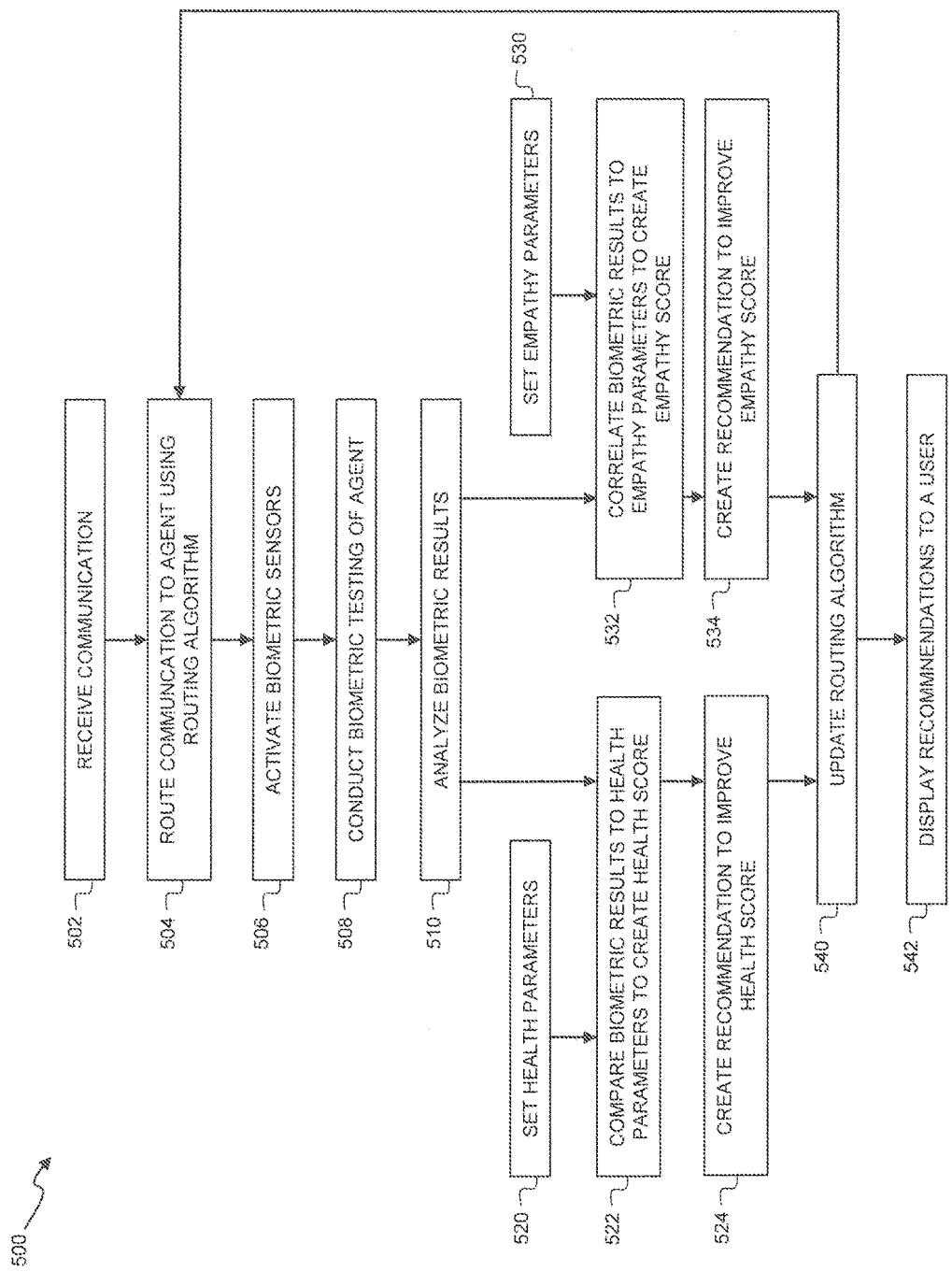
FIG. 5 is a flowchart illustrating an exemplary method of increasing agent health and empathy based on biometric data according to aspects of the present disclosure.

An exemplary method 500 of receiving biometric measurements of an agent and providing recommendations based on the biometric measurements according to the disclosure is described with respect to FIG. 5. Method 500 may be performed by an analysis system such as the analysis control system 200 of FIG. 2.

At step 502, the method 500 may include receiving a communication. In some embodiments, the communication is received by an analysis system such as analysis system 100 of FIG. 1. The communication may be any kind of internet-based interaction, video-based interaction and/or telephone-based interaction. The communication may include both verbal and nonverbal data. Some or all of the communication may be converted into a digital format. In some embodiments, the communication is received by a customer service center and is directed to one or more agents.

At step 504, the method 500 may include routing the communication to an agent using a routing algorithm. The routing algorithm may be configured to route the communication based on a number of factors, including relative workloads of the agents, skill sets of the agents, type of communication, urgency, existing relationships with agents, and other factors. In some embodiments, the routing algorithm may be configured to take into account biometric measurements of agents. For example, communications may be routed to an agent whose biometric measurements indicate that he or she has a low stress level.

At step 506, the method 500 may include activating biometric sensors. These biometric sensors may include sensors that collect biometric information from a user. In some embodiments, the biometric sensors may include the biometric measurement device 180 as depicted in FIG. 1 or the biometric measurement device 300 as depicted in FIG. 3. Some or all of the biometric sensors may be included on a wearable device such as a wristband.

At step 508, the method 500 may include conducting biometric testing of an agent using the biometric sensors. In some embodiments, the biometric sensors are activated during the time that an agent interacts with the communication. The biometric sensors may also be activated before the communication is routed to the agent. For example, the biometric sensors may provide ongoing measurement throughout a work day, including down time and periods when the agent is responding to communications. The biometric sensors may also collect data during interactions between the agents and others, such as clients and other agents. The biometric sensors may be configured to assess the performance of the agent while completing a task. In particular, the biometric testing may include collecting biometric measurements such as blood pressure, heart rate, heart rate variability, breath rate, blood oxygen levels, electrocardiogram (EKG) readings, functional magnetic resonance imaging (FMRI) readings, skin temperature, skin conductance, facial expressions, and other measurements. The biometric measurements received from the biometric testing may be sent to an analysis system for analysis.

At step 510, the method 500 may include analyzing the biometric results. This step may include collecting biometric measurements from the various biometric sensors and comparing them. The analysis may include correlating biometric measurements collected during the biometric testing of step 508 to the wellbeing of the agent. For example, biometric measurements of an agent may be collected during a work day. An elevated heart rate, low blood oxygen levels, and high skin conductance may be measured during the end of the day. These biometric measurements may show that the agent is stressed.

At step 520, the method may include setting health parameters. In some embodiments, health parameters may include targets to compare the biometric measurements to. For example, the health parameters may include a resting heart rate of 70 beats per minute and a blood pressure of 120/80. In some embodiments, the health parameters may be set to reflect a base line for each of the biometric measurements.

At step 522, the method 500 may include comparing the biometric results of 510 to the health parameters of step 520 to create a health score. The health score may reflect the overall health of an agent as well as temporary health states. For example, the health score of an agent may state that he has good overall health (for example, based on heart rate, pulse rate, and blood oxygen levels), but is currently exhibiting signals of tension and stress (for example, based on skin conductance and facial expression analysis). The health score may be compared to base line health scores as well as being compared to the health scores of other agents.

At step 524, the method 500 may include creating a recommendation to improve the health score. In some embodiments, the recommendation is made to correct one or more negative biometric measurements. The recommendations may also include prompts to improve the agent's basic health level, coaching prompts to reduce stress levels, and/or prompts for more successfully interacting with others or responding to communications. Prompts to improve the agent's health may be directed to improving one or more biometric results. For example, an agent may show a high blood pressure reading and a high heart rate variability during several interactions. A recommendation may be sent to the agent with instructions to take a break. The biometric measurements of the agent may be recorded after the break and compared with earlier measurements to ascertain whether stress levels have improved. The recommendations may also instruct the agent to adjust one or more biometric measurement devices, for example, adjusting a heart rate monitor to obtain a clearer reading. The recommendation may be communicated to others such as the agent's supervisor. The recommendation may also include prompts to help the agent interact more successfully with other individuals. For example, the agent may receive a communication from an individual who is unhappy and difficult to work with, causing the measured stress level of the agent to rise. A recommendation after the communication may include prompts on how to more effectively handle difficult communications in the future along with a recommendation to go for a short walk. As the examples show, the recommendation may include several types of prompts and may change over time to modify, e.g., improve the health and/or performance of the agent. As used herein, the term "prompt(s)" is intended to include coaching advice, tips, feedback, or a combination thereof, to (i) one or more supervisors to coach one or more contact agents, e.g., in person or electronically; (ii) directly to one or more contact agent(s), e.g., automated coaching; or a combination thereof.

At step 530, the method 500 may include setting empathy parameters. These parameters may be related to one or more physical manifestations of empathy, such as those discussed in reference to step 420 of method 400. The empathy parameters may also include user defined parameters. For example, an agent may set goals and metrics for measuring empathy levels, such as setting a goal to listen more closely to contacts.

At step 532, the method 500 may include correlating the biometric results of step 510 to the empathy parameters set in step 530 to create an empathy score. A higher empathy score may be attributed to more empathetic behaviors. The empathy score may include sub-scores such as listening, attentiveness, responsiveness, and emotional correlation.

At step 534, the method 500 may include creating a recommendation to improve the empathy score. Examples of this recommendation may include an instruction to an agent to remove distractions to facilitate better listening and comprehension of communications. Because empathy levels may be correlated with health levels, the recommendation may also include health-related suggestions, such as getting something to eat or drink, or taking a break. The recommendation may also include education information about empathy. For example, the recommendation may include statistics about empathy and common empathetic behaviors. In some embodiments, the recommendation is part of a game-based system designed to educate customer service center agents and others. The recommendation may provide a personalized analysis of empathy, which may be presented with background information about empathy and empathetic behaviors.

At step 540, the method 500 may include updating the routing algorithm. In some embodiments, the routing algorithm may be updated to reflect the health and empathy recommendations created in steps 524 and 534, respectively. For example, a health recommendation may be created suggesting that the agent take a 30 minute break due to a high pulse rate. The routing algorithm may be updated to prevent communications from being sent to the agent during the 30 minute break.

At step 542, the method 500 may include displaying the recommendations to a user. The recommendations may be sent to the agent as well as others, such as a supervisor, as well as to an agent database. In some embodiments, the recommendations are displayed on a display device such as display 190 of FIG. 1 or display component 292 of FIG. 2. In some embodiments, the method 500 may repeat itself after step 542, for example, beginning at step 502.

In view of the present disclosure, it will be appreciated that various methods, devices, computer readable media, and systems have been described according to one or more embodiments for receiving biometric measurements of an agent and identifying relationships between the biometric measurements, and the health and/or performance of the agent. These relationships may then be used to route communications to the agent and improve the performance and heath of the agent.

Where applicable, various embodiments provided by the present disclosure may be implemented using hardware, software, or combinations of hardware and software. Also where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the spirit of the present disclosure. In addition, where applicable, it is contemplated that software components may be implemented as hardware components, and vice-versa.

Software in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The various features and steps described herein may be implemented as systems comprising one or more memories storing various information described herein and one or more processors coupled to the one or more memories and a network, wherein the one or more processors are operable to perform steps as described herein, as non-transitory machine-readable medium comprising a plurality of machine-readable instructions which, when executed by one or more processors, are adapted to cause the one or more processors to perform a method comprising steps described herein, and methods performed by one or more devices, such as a hardware processor, user device, server, and other devices described herein.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes, systems, and structures for carrying out the same purposes and/or achieving the same advantages of the embodiments introduced herein. One of ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to allow a quick determination of the nature of the technical disclosure. It is submitted with the understanding that it will not be used to interpret or limit the scope or meaning of the claims.

What is claimed is:

1. A computer-implemented method of routing a communication with a customer in a customer service center, which comprises:

routing a plurality of customer communications to a customer service agent;

activating an electronic wristband comprising a biometric sensor, the electronic wristband being associated with the agent when the communications are routed to the agent;

measuring biometric data, by the biometric sensor, associated with the agent during the communications;

applying a linguistic-based psychological behavioral model to each of the communications to determine a personality type of each customer;

receiving, by a processor, the measured biometric data for the agent and the personality type of each customer;

creating a biometric analysis based on comparing the measured biometric data to a plurality of biometric data targets;

determining a performance score based on the agent's performance in interacting with each customer during the communications, the performance score comprising response time, quantity of interactions, rate of interactions, and quality survey results;

setting at least one empathy parameter;

correlating the measured biometric data to the at least one empathy parameter to create an empathy score;

comparing the empathy score to the performance score;

providing an empathy recommendation based on a comparison of the empathy score to the performance score, wherein the empathy recommendation is based on increasing the empathy score;

updating a routing recommendation for a future communication with a customer based on the empathy recommendation such that the future communication is routed to an agent having a higher empathy score for a personality type of the customer than other selected agents; and routing the future communication based on the updated routing recommendation.

2. The method of claim 1, wherein the measured biometric data include one or more of a blood pressure, a heart rate, a heart rate variability, a blood oxygen level, an electrocardiogram (EKG) reading, a skin temperature, and a skin conductance.

3. The method of claim 1, which further comprises displaying a performance score to a user.

4. The method of claim 1, which further comprises displaying the routing recommendation to a user.

5. The method of claim 1, which further comprises distributing the routing recommendation to a contact center for routing a customer to an agent during one or more future communications.

6. The method of claim 1, further comprising correlating the empathy score to a health score of the agent.

7. The method of claim 1, further comprising determining a stress level of the agent from comparing the measured biometric data to the plurality of biometric data targets.

8. The method of claim 7, wherein the measured biometric data includes a blood pressure and a heart rate, and the plurality of biometric data targets include a resting heart rate of 70 beats per minute and a blood pressure of 120/80.

9. The method of claim 7, wherein the updated routing recommendation is further based on the stress level of the agent.

10. The method of claim 1, further comprising:
determining a personality type of the agent; and
comparing the personality type of the agent to the personality type of the customer in the future communication, wherein the updated routing recommendation is further based on the comparison of personality types.

11. A computer-implemented method for creating recommendations to route a future communication to a contact center agent, which comprises:
routing one or more customer communications with a customer to the agent;
activating an electronic wristband comprising a biometric sensor, the electronic wristband being associated with the agent when the communications are routed to the agent;
measuring biometric data, by the biometric sensor, associated with the agent during the communications;
applying a linguistic-based psychological behavioral model to each of the communications to determine a personality type of each customer;
receiving, by a processor, the measured biometric data for the agent and the personality type of each customer;
determining a performance score based on the agent's performance in interacting with each customer during the communications;
setting at least one empathy parameter;
correlating the measured biometric data to the at least one empathy parameter to create an empathy score;
comparing the empathy score to the performance score;
providing an empathy recommendation based on a comparison of the empathy score to the performance score, wherein the empathy recommendation is based on increasing the empathy score; and
updating a routing recommendation for a future communication with a customer based on the empathy recommendation such that the future communication is routed to an agent having a higher empathy score for a personality type of the customer than other selected agents.

12. The method of claim 11, which further comprises determining a health score based on the biometric data.

13. The method of claim 12, wherein the health score includes a stress level assessment, an overall health assessment, or both.

14. The method of claim 11, wherein the biometric data includes one or more of a blood pressure, a heart rate, a heart rate variability, a blood oxygen level, an electrocardiogram (EKG) reading, a skin temperature, and a skin conductance.

15. The method of claim 11, further comprising correlating the empathy score to a health score of the agent.

16. A system to modify performance of contact center agents based on biometric measurements, which comprises:
an electronic wristband comprising a biometric sensor configured to measure one or more biometric measurements of a contact center agent;
an analysis processor in communication with the electronic wristband, wherein the analysis processor is operably connected to a non-transitory computer readable medium which comprises a plurality of instructions stored in association therewith that are accessible to, and executable by, the analysis processor, wherein the plurality of instructions when executed:
receive, by a processor, the one or more biometric measurements from the electronic wristband comprising the biometric sensor during a plurality of communications with a customer;
apply a linguistic-based psychological behavioral model to each of the plurality of communications to determine a personality type of each customer;
determine a performance score based on the agent's performance in interacting with each customer during the communications;
set at least one empathy parameter;
correlate the measured biometric data to the at least one empathy parameter to create an empathy score;
compare the empathy score to the performance score;
provide an empathy recommendation based on a comparison of the empathy score to the performance score, wherein the empathy recommendation is based on increasing the empathy score;
update a routing recommendation for a future communication with a customer based on the empathy recommendation such that the future communication is routed to an agent having a higher empathy score for a personality type of the customer than other selected agents; and
route the future communication based on the updated routing recommendation.

17. The system of claim 16, further comprising a display device configured to display the one or more biometric measurements to a user.

18. The system of claim 16, wherein the one or more biometric measurements include one or more of a blood pressure, a heart rate, a heart rate variability, a blood oxygen level, an electrocardiogram (EKG) reading, a skin temperature, and a skin conductance.

19. The system of claim 16, wherein the biometric sensor includes one or more of a heart rate monitor, a blood oxygen monitor, an electrodermal analysis (EDA) sensor, a thermometer, an EKG system, and a functional magnetic resonance imaging (FMRI) system.

20. The system of claim 16, wherein the plurality of instructions further comprise instructions that, when executed, correlate the empathy score to a health score of the agent.

* * * * *